United States Patent [19]

Yarchoan et al.

[11] Patent Number: 5,026,687

[45] Date of Patent: Jun. 25, 1991

[54] TREATMENT OF HUMAN RETROVIRAL INFECTIONS WITH 2',3'-DIDEOXYINOSINE ALONE AND IN COMBINATION WITH OTHER ANTIVIRAL COMPOUNDS

[75] Inventors: Robert Yarchoan, Bethesda; Hiroaki Mitsuya, Rockville; Samuel Broder, Bethesda, all of Md.

[73] Assignee: The United States of America as represented by the Department of Health and Human Services, Washington, D.C.

[21] Appl. No.: 460,490

[22] Filed: Jan. 3, 1990

[51] Int. Cl.$^5$ .............................. A61K 31/70
[52] U.S. Cl. ........................ 514/45; 514/50; 514/43; 514/81; 514/637; 536/23; 536/24
[58] Field of Search ............... 514/45, 116; 536/24, 536/26

[56] References Cited

U.S. PATENT DOCUMENTS

| | | | |
|---|---|---|---|
| 3,817,982 | 6/1974 | Verheyden et al. | 536/24 |
| 4,704,357 | 11/1987 | Mitsuya et al. | 435/32 |
| 4,861,759 | 8/1989 | Mitsuya et al. | 514/46 |

FOREIGN PATENT DOCUMENTS 0206497 12/1986 European Pat. Off. .
0302760  2/1989 European Pat. Off. .
62-01284  3/1987 Japan .

OTHER PUBLICATIONS

Johnson et al., J. Biol. Chem., 263(30), 15354-15-357 (1988).
Lee et al., Antimicrobial Agents and Chemotherapy, 33(3), 336-339 (1989).
Tavares et al., Chem. Abstr., 110(23): 204,955q (6/6/89).
Hao et al., Chem. Abstr., 109(25): 222009t (12/19/88).

*Primary Examiner*—Johnnie R. Brown
*Assistant Examiner*—L. Eric Crane
*Attorney, Agent, or Firm*—Birch, Stewart, Kolasch & Birch

[57] ABSTRACT

A preferred method and dosages for the short and long-term treatment of human retroviral infections, or retroviral-like infections, including acquired immunodeficiency syndrome (AIDS) and other manifestations of human immunodeficiency virus (HIV) infection, with 2',3'-dideoxyinosine (ddl) are disclosed, along with a protocol for halting and restarting 2',3'-dideoxyinosine to minimize certain side effects.

27 Claims, No Drawings

TREATMENT OF HUMAN RETROVIRAL INFECTIONS WITH 2',3'-DIDEOXYINOSINE ALONE AND IN COMBINATION WITH OTHER ANTIVIRAL COMPOUNDS

FIELD OF THE INVENTION

This invention relates to the dosages for treatment of human retroviral diseases, particularly for diseases requiring long-term therapy such as HIV infection, with 2',3'-dideoxyinosine (ddI). The invention also relates generally to a protocol for evaluating when the administration of ddI can be restarted if its administration is halted because of treatment-induced neuropathy, pancreatitis, or hepatitis.

BACKGROUND OF THE INVENTION

Human immunodeficiency virus (HIV) is a prototype for pathogenic human retroviruses (i.e. viruses which utilize reverse transcription to replicate). Reverse transcription refers to a process mediated inside a cell by a viral DNA polymerase which can catalyze the flow of genetic information from RNA to DNA. The knowledge, protocols, and teachings pertaining to the avoidance of neuropathy, pancreatitis, and hepatitis with 2',3'-dideoxyinosine as an anti-HIV agent are useful not only for AIDS-like illnesses, but also for 2',3'-dideoxyinosine-treatable illnesses caused by other human viruses which use wholly or in part reverse transcriptase mechanisms to replicate. This includes HTLV-1, HTLV-2, HTLV-V, HIV-2, and hepatitis B virus.

Human immunodeficiency virus (HIV) infection causes a number of clinical abnormalities that can lead to death. The diseases caused by HIV can be treated by certain drugs, including 3'-azido-2',3'-dideoxythymidine (AZT, zidovudine). However, each therapeutically useful drug may be significantly limited in its therapeutic application in human beings by specific toxicities and side-effects. In this regard, since AZT is the only drug now approved specifically for anti-retroviral therapy, it is worth focusing on AZT by way of introduction. AZT causes anemia, other bone marrow suppression, and certain other toxicities such as myositis (muscle destruction or inflammation), headaches, nausea, vomiting, malaise, or seizures. AZT is not known to cause pancreatitis or a peripheral neuropathy, but can cause hepatic dysfunction. Such toxicities and side effects of a drug become crucial factors for optimizing therapy when using a given drug.

The toxicities and side effects caused by a drug in human beings cannot reliably be predicted from in vitro or animal (pre-clinical) studies. For certain toxicities, for example neuropathy and pancreatitis, no tissue culture model exists. Also, reliable extrapolation of specific toxicities from one drug to another is not possible for purposes of drug selection or dose optimization. Moreover, Phase I studies in humans using dose-escalating clinical tests to assess toxicity profiles do not provide teachings about long-term toxicities, nor do such Phase I studies disclose how to manage and avoid such toxicities and side-effects. These considerations become particularly important when very long term therapy is contemplated. HIV therapy is now thought to be a life-long process. Thus, while any prolongation of life or alleviation of suffering is important, it is crucial to develop methods for successfully administering new therapies for long periods of time. In addition to our ability to predict acute toxicities, no method for predicting the overall long-term toxicity profile of a new drug currently exists, particularly when the drug is used for very long-term therapy. Also, once a patient develops a toxicity or adverse reaction, there is often no teaching of methods to predict whether the patient may be safely and effectively re-started on the new drug. The physician and patient would then surely be grateful for the clinical improvement up until the time of an adverse reaction, but would not have guidance as to what to do next. Without such teachings, the possibility of a lethal or incapacitating adverse reaction always looms on the horizon. Having the ability to suppress viral replication with minimal toxicities for very long periods represents a significant addition to a physician's armamentarium.

AZT, discussed above, is the only compound approved for antiretroviral therapy, but to date, no curative therapy exists and many patients cannot tolerate long-term AZT therapy. Furthermore, in some patients, disease processes progress in the face of AZT therapy for any of several reasons, possibly including the development of AZT-resistant strains of the AIDS virus. In addition, the overall cost of therapy presents serious challenges in continued use for many patients.

2',3'-Dideoxyinosine is also known to suppress retroviral replication and thereby benefit an infected host, and initial clinical trials have been reported which demonstrate its efficacy. However, there are currently no teachings or protocols which guide the physician in using 2',3'-dideoxyinosine for very long periods of time, or which prevent or ameliorate serious and unpredictable side effects. In addition, no teachings or protocols exist for the use of this drug on a chronic basis for patients who have already developed a side effect due to 2',3'-dideoxyinosine and in whom the physician wishes to suspend and later restart administration of the drug. Moreover, there are no teachings or protocols for long-term use of 2',3'-dideoxyinosine in patients who have failed currently approved therapy, whose strain of human immunodeficiency virus has become resistant to AZT, or who cannot tolerate AZT.

Relevant citations are provided below, the disclosures of which are incorporated herein by reference in their entirety:

1. Mitsuya, H., Broder, S. Inhibition of the in vitro infectivity and cytopathic effect of human T-lymphotropic virus type III/lymphadenopathy virus-associated virus (HTLV-III/LAV) by 2',3'-dideoxynucleosides. Proc. Natl. Acad. Sci. USA 1986; 83:1911-1915.

2. Mitsuya, H., Weinhold, K. J., Furman, P. A., St. Clair, M. H., Nusinoff Lehrman, S., Gallo, R. C., Bolognesi, D., Barry, D. W., Broder, S. 3'-Azido-3'-deoxythymidine (BW A509U): an antiviral agent that inhibits the infectivity and cytopathic effect of human T-lymphotropic virus type III/lymphadenopathy-associated virus in vitro. Proc. Natl. Acad. Sci. USA 1985; 82:7096-7100.

3. Yarchoan, R., Klecker, R. W., Weinhold, K. J., Markham, P. D., Lyerly, H. K., Durack, D. T., Gelmann, E., Lehrman, S. N., Blum, R. M., Barry, D. W., Shearer, G. M., Fischl, M. A., Mitsuya, H., Gallo, R. C., Collins, J. M., Bolognesi, D. P., Myers, C. E., Broder, S. Administration of 3'-azido-3'-deoxythymidine, an inhibitor of HTLV-III/LAV replication, to patients with AIDS or AIDS-related complex. Lancet 1986; 1:575-580.

4. Yarchoan, R., Perno, C. F., Thomas, R. V., Klecker, R. W., Allain, J.-P., Wills, R. J., McAtee, N., Fischl, M. A., Dubinsky, R., McNeely, M. C., Mitsuya, H., Pluda, J. M., Lawley, T. J., Leuther, M., Safai, B., Collins, J. M., Myers, C. E., Broder, S. Phase I studies of 2',3'-dideoxycytidine in severe human immunodeficiency virus infection as a single agent and alternating with zidovudine (AZT). Lancet 1988; 1:76–81.

5. Yarchoan, R., Broder, S. Development of antiretroviral therapy for the acquired immunodeficiency syndrome and related disorders. A progress report. New Engl. J. Med. 1987; 316:557–564.

6. Yarchoan, R., Mitsuya, H., Myers, C. E., Broder, S. Clinical pharmacology of 3'-azido-2',3'-dideoxythymidine (zidovudine) and related dideoxynucleosides. N. Engl. J. Med. 1989; 321:726–738.

7. Yarchoan, R., Mitsuya, H., Thomas, R. V., Pluda, J. M., Hartman, N. R., Perno, C.-F., Marczyk, K. S., Allain, J.-P., Johns, D. G., Broder, S. In vivo activity against HIV and favorable toxicity profile of 2',3'-dideoxyinosine. Science 1989; 245:412–415.

8. Butler, K., J. Eddy, M. Einloth, P. Jarosinski, H. Moss, P. Wolters, P. Brouwers, L. Weiner, F. M. Balis, D. G. Poplack & P. A. Pizzo. 1989. Dideoxyinosine (ddI) in children with symptomatic HIV infection. A Phase I-II study. In: Program and Abstracts of the Twenty-Ninth Interscience Conference on Antimicrobial Agents and Chemotherapy, Houston, Tex., Sept. 17-20, 1989. 106.

9. Cooley, T., C. A. Saunders, C. J. Perkins, R. P. McCaffery, C. McLaren & H. A. Liebman. 1989. Phase I study of 2',3'-dideoxyinosine (ddI) given once daily to patients with AIDS or ARC. In: Abstracts, V International Conference on AIDS, Montreal, Canada, June 4-9, 1989. 336.

10. Lambert, J., R. Dolin, M. Seidlin, C. Knupp, C. McLaren & R. C. Reichman. 1989. Phase I study of 2',3'-dideoxyinosine (ddI) administered twice daily to patients with AIDS/AIDS related complex. In: Abstracts, V International Conference on AIDS, Montreal, Canada, June 4-9, 1989. 563.

11. Lambert, J. S., R. Dolin, M. Seidlin, C. Knupp, G. Morse, C. McLaren, C. Plank & R. C. Reichman. 1989. 2',3'-Dideoxyinosine (ddI) administered twice daily to patients with AIDS/ARC. In: Program and Abstracts of the Twenty-Ninth Interscience Conference on Antimicrobial Agents and Chemotherapy, Houston, Tex., Sept. 17-20, 1989. 105.

12. Yarchoan, R., R. V. Thomas, H. Mitsuya, C.-F. Perno, J. M. Pluda, N. R. Hartman, D. G. Johns & S. Broder. 1989. Initial clinical studies of 2',3'-dideoxyadenosine (ddA) and 2',3'-dideoxyinosine (ddI) in patients with AIDS or AIDS-related complex (ARC). J. Cell. Biochem. Supplement 13B: 313.

13. Yarchoan, R., R. V. Thomas, J. M. Pluda, N. R. Hartman, H. Mitsuya, C. F. Perno. D. G. Johns & S. Broder. 1989. Escalating dose Phase I study of intravenous and oral 2',3'-dideoxyinosine (ddI) in patients with AIDS or ARC. In: Abstracts, V International Conference on AIDS, Montreal, Canada, 1989. 212.

14. Martin, P., C. Kassianides, J. Korenman, J. N. Hoofnagle, H. Ford, S. Broder, & H. Mitsuya. 1989. 2',3'-Dideoxyinosine (ddI) and dideoxyguanosine (ddG) are potent inhibitors of hepadnaviruses in vivo. In: Program, Digestive Disease Week, Washington, D.C., May 13-17, 1989. A-3.

15. Letter to Physicians from the National Institutes of Health (National Institute of Allergy and Infectious Diseases and the National Cancer Institute), describing the Phase II trials, Treatment IND, and Open Label Protocol for ddI. Mailed Nov. 1, 1989.

16. Mitsuya, H., et al. U.S. Pat. No. 4,861,759. Aug. 29, 1989. Antiviral compositions and methods.

SUMMARY OF THE INVENTION

The present invention relates to a method of alleviating diseases caused by viruses that replicate by reverse transcription through the administration of 2',3'-dideoxyinosine (ddI) in a dosage range of about 0.4 to about 25.6 mg/kg/day. The invention further relates to the foregoing method wherein the ddI is administered intravenously or orally.

Additional aspects of the present invention relate to a method for increasing the CD4+ count as well as increasing the CD4+:CD8+ ratio in immunodepressed patients suffering from a disease caused by viruses that replicate by reverse transcription by administration of ddI in a dosage range of about 0.4 mg/kg/day to about 25.6 mg/kg/day. Other aspects of the present invention also relate to a more preferred dosage range of about 1.0 to about 14 mg/kg/day, with a most preferred dosage range of about 6.4 to about 9.6 mg/kg/day.

Other aspects of the present invention include a method of administering ddI to a patient infected with HIV or other diseases caused by viruses that replicate by reverse transcription in a manner to minimize neuropathy, pancreatitis and hepatitis by monitoring certain clinical parameters and temporarily halting ddI administration until these parameters return to or near baseline and then restarting therapy. Additional aspects include the administration of ddI in multiple dosages per day, such as 1 to about 3 doses per day.

Yet another aspect of the present invention relates to a method of treating HIV-induced dementia through the administration of effective amounts of ddI.

Other aspects of the present invention include the clinical administration of combinations of ddI along with other antiviral or immunological response modifiers including lymphokines and cytokines.

Further aspects of the present invention include pharmaceutical compositions formulated to deliver in unit dosage form the preferred dosages discussed above.

DETAILED DESCRIPTION OF THE INVENTION

The present invention relates to a protocol for determining when the onset of treatment-induced peripheral neuropathy, pancreatitis, or hepatitis requires a halt in treatment so as to optimize the prospects for restarting a patient on that treatment without acutely precipitating the same neuropathy, pancreatitis, or hepatitis. This general protocol particularly contemplates 2',3'-dideoxyinosine and related compounds, but may be applicable for any therapeutic compound to treat any disease, when for such compounds neuropathy, pancreatitis, or hepatitis are toxic side effects. The present invention further relates to protocols which optimize the efficacy of and avoid the toxicities associated with the treatment of humans infected with an RNA virus, such as human immunodeficiency virus, or a DNA virus, such as hepatitis B virus, which utilizes a retroviral mechanism (reverse transcription) in part to replicate. Use of this protocol does not guarantee that a given drug may be restarted successfully after the initial onset of neuropathy, pancreatitis, or hepatitis; however, the protocol may optimize the chances for successful restarting of the therapy. Actual clinical administration will be required for each compound in order to determine whether administration of the compound may be restarted beneficially.

A preferred embodiment of the present invention relates to the determination of optimal initial dosing for 2',3'-dideoxyinosine administered as an anti-HIV therapeutic so as to lessen the risk of an adverse reaction or side-effect to begin with. This preferred embodiment is also preferred for long-term therapy with 2',3'-dideoxyinosine. Methods and protocols for restarting 2',3'-dideoxyinosine following an adverse reaction are now disclosed.

As an example of a toxicity-avoiding protocol, tests with 2',3'-dideoxyinosine in patients with acquired immunodeficiency syndrome (AIDS), AIDS-related complex, or other manifestations of human immunodeficiency infection have shown the therapeutic benefit discussed below. At certain dosage regimens, however, toxicity becomes a significant patient management problem.

The administration of 2',3'-dideoxyinosine by the intravenous or oral route is associated with an increase in weight, an increase in energy, an improvement in cognitive dysfunction associated with human immunodeficiency virus infection, a reduction of the amount of p24 antigen of the AIDS virus detectable in serum, an increase in the number of circulating lymphocytes, and improvement in immune function, for long periods of time. As manifestations of improvement in immune function, patients with human immunodeficiency virus infection who were administered 2',3'-dideoxyinosine had an increase in the number of circulating total lymphocytes, an increase in the number of circulating CD4+ lymphocytes, an increase in the ratio of CD4+ to CD8+ lymphocytes, and an increase in the number of CD8+ lymphocytes. In addition, some patients who were anergic before being given 2',3'-dideoxyinosine (that is, they did not mount a cutaneous delayed type hypersensitivity reaction to test antigens) regained the ability to mount a cutaneous delayed type hypersensitivity reaction to at least one test antigen.

It has now been discovered that the foregoing clinical improvements can persist over at least a year's period of time, and that they can be observed with a preferred dosage of about 2 mg/kg/day to about 14 mg/kg/day of 2',3'-dideoxyinosine administered orally with antiacids or buffers.

It has been further discovered that these beneficial effects can be seen at higher doses of 2',3'-dideoxyinosine (that is, more than about 14 mg/kg/day of 2',3'-dideoxyinosine given orally with antiacids or buffers, or the equivalent), but that at those doses, toxicity often develops in the context of very long-term therapy, i.e., periods of administration longer than one year. It has been discovered that the most common serious toxicities at these higher doses are pancreatitis or other pancreatic dysfunction, neuropathy such as painful or numb feet, and hepatitis. These specific side-effects and toxicities of this drug were previously unknown. It has been discovered that the incidence of these toxicities surprisingly can be reduced by administering lower initial doses of ddI (about 2 mg/kg/day to about 14 mg/kg/day of 2',3'-dideoxyinosine given orally with antacids or buffers) divided into as few as 1, 2, 3 doses per day without sacrificing total cumulative dose. It has also surprisingly been discovered that the administration of 2',3'-dideoxyinosine can be halted temporarily even at the lower preferred dosages and restarted without the acute return of neuropathy, pancreatitis, or hepatitis. Protocols for preventing these toxicities, for restarting 2',3'-dideoxyinosine after a rest period once these toxicities appear, and for managing the toxicities are discussed below.

2',3'-Dideoxyinosine can be administered as a sterile intravenous infusion. When 3.2 mg/kg of 2',3'-dideoxyinosine is administered intravenously over 1½ hr, the peak level of 2',3'-dideoxyinosine is approximately 10 $\mu$M. The circulating half-life of the drug is about 40 minutes. In three patients where this was measured, the concentration of 2',3'-dideoxyinosine in the cerebrospinal fluid averaged approximately 20% of that in the serum 1 hour after an intravenous infusion of 2',3'-dideoxyinosine. The drug can also be administered orally dissolved in water, apple juice, or another suitable aqueous solution. When dissolved in apple juice and given to a fasting patient about 2 minutes after ingestion of an antacid such as 30 cc of aluminum hydroxide suspension or comparable antacid, the bioavailability of 2',3'-dideoxyinosine is approximately 35 to 40%. A similar bioavailability can be attained if 2',3'-dideoxyinosine mixed with a suitable buffer (such as sodium citrate, acetate, or bicarbonate) and a sugar is dissolved in water and administered orally to a fasting patient. Flavorings of various kinds can be added. In three patients where the concentration was measured, the concentration of ddI in the cerebrospinal fluid averaged approximately 20% of that in the serum about 1 hr after an intravenous infusion of 2',3'-dideoxyinosine. The human oral bioavailability of this drug was not predicted because of the extreme acid lability of the N-glycosidic bond. It has previously been shown that 2',3'-dideoxyadenosine can be orally bioavailable in a beagle dog. The present inventors have found that 2',3'-dideoxyinosine can be made orally bioavailable for chronic very long term use in human beings and that the oral absorption and pharmacokinetics of 2',3'-dideoxyinosine remain fairly constant with chronic administration in a given person. Thus, individual patients may handle the drug fairly consistently without a significant alteration in the pharmacologic fate of the drug under the conditions of this protocol.

EXAMPLE 1

Administration of 2',3'-dideoxyinosine

The patients described herein were treated with oral 2',3'-dideoxyinosine administered to the patient in a fasting state. The 2',3'-dideoxyinosine was dissolved in apple juice and administered to the patients about 2 minutes after they had ingested 30 cc of aluminum hydroxide suspension or magnesium hydroxide and aluminum hydroxide suspension. Similar results would be attained with other oral formulations, including cachets, if the doses are corrected to provide for the different oral bioavailability of these different oral formulations. 2',3'-Dideoxyinosine can be absorbed if administered orally as a buffered tablet; as a capsule, for example as an enteric-coated capsule; as an enteric-coated tablet in a long-release form; or an analogous form. 2',3'-Dideoxyinosine is also effectively absorbed by the oral route if the patient is not in a fasting state.

EXAMPLE 2

Optimization of initial 2',3'-dideoxyinosine dosage

In an initial study, 37 patients with AIDS or AIDS-related complex were given 0.4 to 25.6 mg/kg/day of 2',3'-dideoxyinosine intravenously divided into 1, 2, or 3 doses. Some of the patients with AIDS-related complex had the diagnosis made on the basis of having had oral candidiasis, but had no symptoms at the time of treatment. Other patients had fatigue, loss of appetite, fevers, or recent weight loss. Many of these patients could not tolerate therapy with 3'-azido-2',3'-dideoxythymidine (AZT, zidovudine) because of nausea, malaise, or bone marrow toxicity, or were clinically deteriorating while on AZT treatment. It is known from prior art that many patients on long-term AZT therapy develop AZT-resistant mutant forms of HIV or will clinically deteriorate and die despite AZT therapy. After about two weeks of dosing with intravenous 2',3'-dideoxyinosine, 2',3'-dideoxyinosine was given to the patients orally while they were fasting at twice the intravenous dose. For this oral administration, the 2',3'-dideoxyinosine was dissolved in apple juice and ingested about 2 minutes after ingestion of 30 cc of aluminum hydroxide suspension or magnesium hydroxide and aluminum hydroxide suspension.

Of the 37 patients, 35 received the 2',3'-dideoxyinosine for more than 2 weeks and were considered evaluable. Overall, these patients had increases in their circulating CD4+ cells, increases in the ratio of circulating CD4+:CD8+ lymphocytes, increases in the number of CD8+ lymphocytes, and increases in the number of total lymphocytes. Patients on this study also had evidence of a decrease in the replication in their HIV and clinical improvement. The increases in CD4+ lymphocytes were most consistently seen in patients who had previously received 4 months or less of 3'-azido-2',3'-dideoxythymidine (zidovudine, AZT) therapy. However, the benefits of 2',3'-dideoxyinosine administration (including immunologic improvement) were not limited to such patients, and it is disclosed that patients whose disease has progressed or has started to progress in the face of AZT therapy can be treated with 2',3'-dideoxyinosine.

Evaluation of the dosage studies of Example 2

The beneficial changes described above were seen in nearly all of the patients in this study with AIDS or AIDS-related complex who were given a dosing regimen of about 2 to 14 mg/kg/day of 2',3'-dideoxyinosine orally with appropriate buffers or antacid as described above. The beneficial effect of dosing as few as 1, 2, or 3 times a day is remarkable given the short half life of the drug. These patients had first received intravenous 2',3'-dideoxyinosine for about two weeks at half the oral dose. However, it is disclosed that a prior course of intravenous therapy is not a requisite for a beneficial effect of oral therapy using 2',3'-dideoxyinosine.

The patients who received 2',3'-dideoxyinosine at intravenous doses of about 1 to 7 mg/kg/day divided into 1, 2, or 3 daily doses, following by 2',3'-dideoxyinosine given orally at twice the intravenous doses (about 2 to 14 mg/kg/day) generally had substantial increases in the number of circulating CD4+ lymphocytes, increases in the number of circulating CD8+ lymphocytes, increases in the number of circulating total lymphocytes, and increases in the ratio of circulating CD4+:CD8+ lymphocytes. These changes were observed within about 2 weeks, and in many cases were sustained for at least one year.

For example, one patient had about 31 CD4+ lymphocytes/mm$^3$, 189 CD8+ lymphocytes/mm$^3$, 405 total lymphocytes/mm$^3$, and a CD4+:CD8+ ratio of 0.16 before receiving 2',3'-dideoxyinosine. He received about 1.6 mg/kg/day of 2',3'-dideoxyinosine intravenously for about 2 weeks, about 3.2 mg/kg/day of 2',3'-dideoxyinosine orally for about 10 weeks, about 4.8 mg/kg/day of 2',3'-dideoxyinosine orally for about 21 weeks, and about 9.6 mg/kg/day of 2',3'-dideoxyinosine orally for about 31 weeks. At the end of this treatment period, he had about 90 CD4+ lymphocytes/mm$^3$, about 302 CD8+ lymphocytes/mm$^3$, about 816 total lymphocytes/mm$^3$, and a CD4+:CD8+ ratio of about 0.3. As another example, a second patient had about 219 CD4+ lymphocytes/mm$^3$, 844 CD8+ lymphocytes/mm$^3$, 1270 total lymphocytes/mm$^3$, and a CD4+:CD8+ ratio of 0.26 before receiving 2',3'-dideoxyinosine. He received about 4.8 mg/kg/day of 2',3'-dideoxyinosine intravenously for about 2 weeks, followed by about 9.6 mg/kg/day of 2',3'-dideoxyinosine orally. After about one year of therapy, he had about 359 CD4+ lymphocytes/mm$^3$, about 1256 CD8+ lymphocytes/mm$^3$, about 1794 total lymphocytes/mm$^3$, and a CD4+:CD8+ ratio of about 0.29. Of the first 7 patients treated with intravenous doses of 3.2 to 4.8 mg/kg/day of 2',3'-dideoxyinosine intravenously for about 2 weeks, followed by about 6.4 to 9.6 mg/kg/day of 2',3'-dideoxyinosine orally, 4 still had increases in their circulating CD4+ lymphocytes after about one year of therapy.

Improvements in immune parameters have also been observed in patients receiving doses below 2 mg/kg/day of 2',3'-dideoxyinosine orally. However, these improvements were not as consistently seen in patients receiving less than 2 mg/kg/day of 2',3'-dideoxyinosine by the oral route. Some patients who received more than 14 mg/kg/day of 2',3'-dideoxyinosine orally also had improvements in immune parameters, but were more likely to develop toxic effects on long-term use. Patients have manifested improvements whether they have first received intravenous 2',3'-dideoxyinosine or were initially started on oral 2',3'-dideoxyinosine. 17 patients have now received 2',3'-dideoxyinosine with beneficial effects for at least one year. Other patients are now nearing the one year mark, following protocols that are now disclosed.

Of the 37 patients in this study, 26 were anergic at entry; that is, they did not develop a cutaneous delayed type hypersensitivity reaction to candida, 5 test units of purified protein derivative, tetanus, or trichophyton. 23 of these anergic patients were retested after approximately 6 weeks of therapy with 2',3'-dideoxyinosine; of these 23, 7 developed skin test reactivity to at least one test antigen.

A high percentage of patients with detectable serum HIV p24 antigen who received 2',3'-dideoxyinosine at intravenous doses of about 1 to 7 mg/kg/day for about two weeks divided into 1, 2, or 3 daily doses, followed by oral doses (as described above) twice as great (about 2 to 14 mg/kg/day) had substantial decreases in their serum HIV p24 antigen by week 6 of therapy. Of the 7 patients described above who received about 6.4 to 9.6 mg/kg/day of 2',3'-dideoxyinosine orally, 3 had detectable serum HIV p24 antigen before therapy. All 3 had a decline during the first 6 weeks of therapy, and two of these three patients had no detectable serum HIV p24 antigen after about one year of therapy with ddI at an oral dose of about 6.4 to 9.6 mg/kg/day. Patients also had a decrease in the load of HIV in their circulating lymphocytes as detected by polymerase chain reaction while receiving 2′,3′-dideoxyinosine. Clinical improvements have been seen in patients who were viremic in the face of AZT therapy upon their being treated with 2′,3′-dideoxyinosine. These improvements include, but are not limited to, a fall in serum HIV p24 antigen (one marker of in vivo viral replication).

Overall, approximately one half of the 37 patients noted above treated with 2′,3′-dideoxyinosine reported an improvement in well being: specifically, an increase in energy, decreased sleep requirements, or increased appetite. Overall, the patients gained an average of 1.5 kg of weight during the first 6 weeks of therapy.

Cognitive function improved in 4 patients treated with 2′,3′-dideoxyinosine who had human immunodeficiency virus-associated neurological dysfunction prior to therapy. In each case, there was an improvement in memory and in the speed and precision of doing tasks after 6 to 10 weeks of therapy. One of these patients received about 9.6 mg/kg/day of 2′,3′-dideoxyinosine orally, divided into 3 doses. This patient's memory quotient increased from 111 to 121 after 6 weeks of therapy; his speed of completion of the Trailmaking A test increased from 25 to 18 seconds; and his speed of completion of the Trailmaking B test increased from 96 to 80 seconds. The other three patients who had improvement in cognitive function received higher daily doses of 2′,3′-dideoxyinosine. Thus, the protocols and methods now disclosed can ameliorate virally-related dementia.

In addition to the 37 patients mentioned above, another 20 patients have been treated for a total of 57. Five of these patients initially and briefly received 2′,3′-dideoxyadenosine, which has been found to be rapidly converted to 2′,3′-dideoxyinosine in patients.

Combination therapy with other anti-viral or immunopotentiating agents

Patients have been treated using 2′,3′-dideoxyinosine in combination with other anti-viral agents, and other therapies commonly used in the treatment of AIDS and its related disorders and other viral diseases. Examples of such therapies are disclosed in the following examples. It is contemplated that one of ordinary skill in the art will be able to optimize the dosages of such other agents based on the following examples. For example, the use of combination antiretroviral therapy, simultaneously or sequentially, for example alternating drugs about week-by-week or about month-by-month, results in a decreased risk of the emergence of drug resistant variants of viruses in patients. Also, the use of combination antiretroviral therapy, simultaneously or sequentially, for example alternating drugs about week-by-week or about month-by-month, results in diminished toxicity and side effects from each drug as compared to that obtained when the drugs are used singly.

EXAMPLE 3

Administration of 2′,3′-dideoxyinosine and AZT

AZT was synergistic with 2′,3′-dideoxyinosine in vitro when tested for its ability to protect the ATH8 T cell line against the cytopathic effect of HIV. A patient is treated with about 300 mg/day of AZT orally, divided into about 3 doses, simultaneously with about 3.2 mg/kg/day of 2′,3′-dideoxyinosine orally divided into about 3 doses for about one year. Another patient is treated with about 600 mg/day of AZT orally, divided into about 3 doses per day for about one week, followed by about 6.4 mg/kg/day orally of 2′,3′-dideoxyinosine divided into about 3 doses per day for about one week. These two drugs are alternated in this manner about week-by-week for about one year. Beneficial effects are seen. A dose range of about 50 to about 600 mg/day of AZT orally may successfully be used with 2′,3′-dideoxyinosine given in a dose range of about 0.4 mg/kg/day to about 9.6 mg/kg/day, both doses being given orally about three times per day. Note that when the 2′,3′-dideoxyinosine is used simultaneously with AZT, lower doses of 2′,3′-dideoxyinosine and AZT may be used with beneficial effects.

EXAMPLE 4

Administration of 2′,3′-dideoxyinosine and 2′,3′-dideoxycytidine (ddC)

2′,3′-Dideoxycytidine (ddC) was synergistic with 2′,3′-dideoxyinosine in vitro when tested for its ability to protect the ATH8 T cell line against the cytopathic effect of HIV. A patient is treated with about 0.015 mg/kg/day of ddC orally, divided into about 3 doses, in combination with about 3.2 mg/kg/day of 2′,3′-dideoxyinosine orally, divided into about 3 doses per day for about 6 months. Another patient is treated with about 0.03 mg/day of ddC orally, divided into about 3 doses per day for about one week, followed by about 6.4 mg/kg/day orally of 2′,3′-dideoxyinosine divided into about 3 doses per day for about one week. These two drugs are alternated about week-by-week for about 6 months. Beneficial effects are seen. A dose range of about 0.005 to 0.03 mg/kg/day of ddC orally may successfully be used with 2′,3′-dideoxyinosine given in a dose range of about 0.4 mg/kg/day to about 9.6 mg/kg/day, both doses being given orally about three times per day.

EXAMPLE 5

Administration of 2′,3′-dideoxyinosine and acyclovir

A patient with AIDS who has been previously treated with gancyclovir for cytomegalovirus retinitis was treated with about 6.4 mg/kg/day of 2′,3′-dideoxyinosine orally divided into 2 doses per day simultaneously with about 4800 mg/day of acyclovir orally divided into 6 doses per day. After 4 weeks of treatment, the ratio of CD4+ lymphocytes to CD8+ lymphocytes has increased from about 0.02 to about 0.04, and the retinitis has not recurred. A dose range of about 200 to 4800 mg/day of acyclovir may successfully be used with 2′,3′-dideoxyinosine given in a dose range of about 1 to 9.6 mg/kg/day, both doses being given orally about three times per day.

EXAMPLE 6

Administration of 2′,3′-dideoxyinosine and 1,3-dihydro-2-propoxy-methylquanine (DHPG, gancyclovir)

A patient who has been previously treated with gancyclovir for cytomegalovirus retinitis was treated with about 6.4 mg/kg/day of 2′,3′-dideoxyinosine orally divided into 2 doses per day simultaneously with gancyclovir at about 500 mg/day administered by intravenous infusion. After 2 weeks of therapy, the patient reports feeling better, has an increase in weight of about 2.2 kg, and has not had a recurrence of the retinitis. A dose range of about 200 to 1500 mg/kg/day of gancyclovir given about 5 to 7 times per week may successfully be used with 2',3'-dideoxyinosine given in a dose range of about 1 to 9.6 mg/kg/day orally about three times per day.

EXAMPLE 7

Administration of 2',3'-dideoxyinosine and interferon

2',3'-Dideoxyinosine successfully is used in combination with a human interferon preparation (e.g. alpha interferon). An HIV-infected patient with Kaposi's sarcoma is administered a dose in the range of about 1 to 14 mg/kg/day of 2',3'-dideoxyinosine orally divided into 1, 2, or 3 doses per day in combination with about 0.5 to 10 million units of interferon alpha daily given by the subcutaneous route or other routes for about 3 months. Beneficial effects are seen. Such beneficial effects would not be limited to patients with Kaposi's sarcoma.

EXAMPLE 8

Administration of 2',3'-dideoxyinosine with various lymphokines

2',3'-Dideoxyinosine is also used in combination with other lymphokines or cytokines such as interleukin-2 (IL-2) or modified variants of IL-2 to build up the patient's immune system. For example, a patient is given about 1 to 14 mg/kg/day of 2',3'-dideoxyinosine orally divided into 1, 2, or 3 doses per day in combination with about 25,000 to 1 million U/day of IL-2 given by continuous infusion or other systemic administration for about 3 months. Beneficial effects are seen.

2',3'-Dideoxyinosine may be successfully used in human beings who are receiving aerosolized pentamidine, trimethoprim-sulfamethoxazole, or other prophylaxis against Pneumocystis carinii pneumonia or other opportunistic infections.

EXAMPLE 9

Administration of 2',3'-dideoxyinosine with prophylaxis against Pneumocystis carinii pneumonia A patient who previously had had Pneumocystis carinii pneumonia was treated with about 4.8 mg/kg/day of 2',3'-dideoxyinosine intravenously divided into three doses per day for about 2 weeks, followed by about 9.6 mg/kg/day of 2',3'-dideoxyinosine orally divided into three doses per day for about 56 weeks. During his treatment with 2',3'-dideoxyinosine, he also received about 300 mg of pentamidine isothionate delivered by inhalation about every month. During this treatment period, he clinically did well and did not develop Pneumocystis carinii pneumonia. Dosing with about 1 mg/kg/day to about 14 mg/kg/day of 2',3'-dideoxyinosine orally divided into about 1 to 3 daily doses may be used in combination with about 50 mg to about 400 mg of pentamidine isothionate delivered by inhalation about every two weeks to about every month with beneficial effects.

EXAMPLE 10

Administration of 2',3'-dideoxyinosine and recombinant soluble CD4 or its analogues 2',3'-Dideoxyinosine was found to be synergistic in vitro with recombinant soluble CD4 (rCD4) in protecting the helper T cell line ATH8 against the cytopathic effect of HIV. A patient is treated with about 6.4 mg/kg/day of 2',3'-dideoxyinosine orally about 2 times per day in combination with about 300 µg/kg/day of rCD4 by the intravenous route for 1 year. Beneficial effects are seen.

EXAMPLE 11

Administration of 2',3'-dideoxyinosine and anionic polysaccharides, including dextran sulfate 2',3'-Dideoxyinosine was found to be synergistic in vitro with dextran sulfate in protecting the helper T cell line ATH8 against the cytopathic effect of HIV. A patient is treated with about 6.4 mg/kg/day of 2',3'-dideoxyinosine orally about 2 times per day in combination with about 2700 mg/day of dextran sulfate by the intravenous route for about 6 months. Beneficial effects are seen.

EXAMPLE 12

Administration of 2',3'-dideoxyinosine and ribavirin

Ribavirin has been found to induce enhancement of the anti-HIV effect of 2',3'-dideoxyinosine in a T-cell line as measured by the effect on HIV p24 gag production into the supernatant. A dose of about 3.2 mg/kg/day of 2',3'-dideoxyinosine administered orally divided into about 2 daily doses is given with about 100 to 2400 mg/day of ribavirin given orally divided into 1 to 6 daily doses for about 6 months. Beneficial effects are seen.

Minimization of toxicities

Means of avoiding the primary untoward side effects of 2',3'-dideoxyinosine, peripheral neuropathy, pancreatitis, and hepatitis, could not have been predicted from the use of AZT since the toxicology of AZT is different, though surely as serious. Hence, means of preventing and managing these toxicities to enable 2',3'-dideoxyinosine to be administered for years in at least some patients has been needed. This is an important aspect of this invention.

The peripheral neuropathy from 2',3'-dideoxyinosine appears as a sensation of pain, tingling, or numbness in the feet or other body parts of patients. It has now been discovered that the daily dose of 2',3'-dideoxyinosine (dose intensity) is an important variable in the development of the neuropathy.

EXAMPLE 13

Effect of total dose and dose intensity on the development of 2',3'-dideoxyinosine-induced neuropathy If patients received less than a cumulative total dose of about 1.5 gm/kg of 2',3'-dideoxyinosine or if they received about 2 mg/kg/day to about 9.6 mg/kg of 2',3'-dideoxyinosine per day orally, the neuropathy was much less likely to appear. When a dose of about 2 mg/kg/day to about 9.6 mg/kg/day of 2',3'-dideoxyinosine was used, a cumulative dose of 1.5 gm/kg was exceeded during dosing of about 1 to 1½ years or more in many patients without neuropathy appearing. However, one may wish to use a higher dose of 2',3'-dideoxyinosine for therapy of certain manifestations of HIV infection. For example, one may wish to treat a patient with HIV-related dementia with about 14 mg/kg/day of 2',3'-dideoxyinosine. Neuropathy is less likely to occur if such treatment is stopped when a cumulative dose of 1.5 gm/kg is reached. After a rest period of about a month, 2',3'-dideoxyinosine may be restarted at about 2 to 9.6 mg/kg/day orally. Restarting 2',3'-dideoxyinosine after the development of neuropathy will be discussed below. As has been taught above, HIV-related dementia may be successfully treated with lower doses of 2',3'-dideoxyinosine than 14 mg/kg/day, for example with about 9.6 mg/kg/day of 2',3'-dideoxyinosine orally.

It was discovered that if 2',3'-dideoxyinosine was stopped when a patient experienced loss of vibratory sense or pain or tingling of mild to moderate severity lasting for several hours (warning phase), the neuropathy subsided if the 2',3'-dideoxyinosine was promptly stopped. Furthermore, when the neuropathy subsided, the 2',3'-dideoxyinosine could again be administered at a dose of about 2 to 9.6 mg/kg/day orally. In more than half the patients, this second dosing could be continued without serious neuropathy appearing. One expectation, prior to the current invention, was that re-starting the drug would worsen or aggravate the neuropathy, making such an intervention dangerous to the patient. It is now possible to successfully restart ddI treatment of such patients. As part of this teaching, failure to identify incipient neuropathy in its warning phase and to follow the disclosure of the present invention can lead to an intractable and incapacitating pain syndrome. This pain syndrome may not be amenable to any known therapy once it comes into force.

EXAMPLE 14

Restarting 2',3'-dideoxyinosine in a patient who has developed 2',3'-dideoxyinosine-induced neuropathy.

A patient developed neuropathy after receiving about 19.2 mg/kg/day of 2',3'-dideoxyinosine intravenously divided into 3 daily doses for about 2 weeks, followed by about 38.4 mg/kg/day of 2',3'-dideoxyinosine orally divided into 3 daily doses for about 5 weeks. The 2',3'-dideoxyinosine was held for about 4 months. The 2',3'-dideoxyinosine was then administered at a dose of about 9.6 mg/kg/day orally divided into 3 daily doses for about 10 weeks, followed by about 6.4 mg/kg/day orally divided into 2 daily doses for about 10 weeks. The neuropathy did not recur during the 20 week period after the 2',3'-dideoxyinosine was restarted.

EXAMPLE 15

Minimizing pancreatic toxicity.

From prior art and general medical teaching, it is known that pancreatitis can be a serious and possible lethal condition. No prior art or teachings exist regarding the prevention or amelioration of this adverse reaction following the administration of 2',3'-dideoxyinosine. Similarly, no prior art or teachings exist for re-starting a patient on this drug once pancreatitis has occurred. For example, 6-mercaptopurine, used to treat inflammatory bowel disease, causes pancreatitis that returns acutely if even low doses of this compound are administered after a patient has developed pancreatitis. Absent such teachings and protocols, physicians would find it very problematic to practice the use of 2',3'-dideoxyinosine. The findings of the present inventors are quite surprising given the conventional experience with previous drugs.

It was discovered that 2',3'-dideoxyinosine can definitely cause pancreatitis at certain doses. It was further discovered that 2',3'-dideoxyinosine-induced pancreatitis can sometimes be preceded by a rise in serum triglyceride levels. This rise can be without symptoms in the patient. By measuring the serum triglyceride levels about every 1 to 2 weeks and temporarily stopping 2',3'-dideoxyinosine when it exceeds about 500 mg/dl in patients with normal starting levels, the incidence of 2',3'-dideoxyinosine-induced pancreatitis can be reduced. Also, the incidence of 2',3'-dideoxyinosine-induced pancreatitis can be reduced by administering oral doses of about 2 to 14 mg/kg/day. It was further discovered that patients who have elevated serum pancreatic amylase levels while receiving 2',3'-dideoxyinosine may be clinically asymptomatic. The 2',3'-dideoxyinosine can be temporarily discontinued upon a rise in the serum amylase levels of about 150% or more of the upper limit of normal in a given hospital's clinical lab until the amylase returns to normal or near normal. Such a return to about normal levels usually occurs in about one week. The 2',3'-dideoxyinosine may then be restarted at an oral dose of about 2 to 9.6 mg/kg/day without necessarily reinducing a rise in serum amylase.

EXAMPLE 16

Managing patients who develop an elevated serum amylase level while receiving 2',3'-dideoxyinosine.

A patient received about 9.6 mg/kg/day of 2',3'-dideoxyinosine orally divided into 3 daily doses for about 12 weeks. When he started on therapy, his serum amylase was about 67 U/liter (top normal value about 94 U/liter in that particular laboratory). By about week 12, his amylase had increased to about 207 U/liter, but he had no clinical symptoms of pancreatitis. His 2',3'-dideoxyinosine was temporarily stopped for about 1 week, during which time the amylase fell to about 137 U/liter. The 2',3'-dideoxyinosine was then restarted at about 6.4 mg/kg/day orally divided into 2 daily doses. Three weeks after the 2',3'-dideoxyinosine was restarted, he still had no evidence of pancreatitis, and his serum amylase level was 80 U/liter.

In patients who develop symptomatic pancreatitis, the drug should be stopped until symptoms have resolved and the level of circulating amylase has normalized. 2',3'-Dideoxyinosine can then be resumed at an oral dose of about 2 mg/kg/day to about 9.6 mg/kg/day, preferably at about one-half or less of the previous dose, without necessarily reinducing pancreatitis. Such a capacity to re-start this drug differs from the experience with other pancreatitis-inducing drugs, and is quite surprising.

EXAMPLE 17

Restarting 2',3'-dideoxyinosine in a patient who has developed 2',3'-dideoxyinosine-related pancreatitis.

A patient received 2',3'-dideoxyinosine at a dose of 9.6 mg/kg/day intravenously divided into 3 daily doses for about 2 weeks, followed by 19.2 mg/kg/day orally divided into 3 daily doses for about 12 weeks. At that time, he developed pancreatitis with abdominal pain, nausea, and vomiting and his serum amylase had increased to over four times the upper limit of normal. The drug was discontinued and he received supportive and symptomatic therapy for the pancreatitis. About 15 weeks later, he was restarted on 2',3'-dideoxyinosine at a dose of about 6.4 mg/kg/day orally, divided into 2 daily doses. Pancreatitis did not recur during the next 7 weeks during which he was receiving 2′,3′-dideoxyinosine.

EXAMPLE 18

Minimizing hepatic toxicity.

Similar methods and protocols may be applied to minimize the development of 2′,3′-dideoxyinosine-related hepatitis. Patients should have their hepatic transaminases monitored about every 2 to 3 weeks, and the 2′,3′-dideoxyinosine should be temporarily discontinued when the transaminases exceed five times the upper limits of normal or the patient develops frank hepatitis. In the case of transaminase elevations or hepatitis, it is possible to re-start use of the drug. However, use of 2′,3′-dideoxyinosine should be delayed until abnormal liver functions decrease to about three times the upper limit of normal. The drug may then be restarted at a dose of about 2 mg/kg/day to about 9.6 mg/kg/day orally, preferably at about one-half or less of the previous dose.

EXAMPLE 19

Restarting 2′,3′-dideoxyinosine in a patient who has developed 2′,3′-dideoxyinosine-related hepatitis.

A patient received 2′,3′-dideoxyinosine at a dose of 6.4 mg/kg/day intravenously divided into 2 daily doses for about 2 weeks, followed by 12.8 mg/kg/day orally divided into 3 daily doses for 14 weeks. At that time, he developed frank hepatitis with abdominal pain, malaise, and elevations of hepatic transaminases. The 2′,3′-dideoxyinosine was discontinued, and he received symptomatic therapy for his hepatitis. Over the next several weeks, the hepatitis resolved. About 8 weeks after the 2′,3′-dideoxyinosine was discontinued, the 2′,3′-dideoxyinosine was restarted at a dose of about 6.4 mg/kg/day orally divided into 2 doses. The hepatitis did not recur during at least 20 weeks of this retreatment.

Using the dosing regimens and methods revealed above for preventing and managing the toxicities from 2′,3′-dideoxyinosine, 17 patients have received 2′,3′-dideoxyinosine with beneficial effects for at least one year. Many of these patients have received 2′,3′-dideoxyinosine therapy well in excess of a year. Others are nearing the one-year mark.

It is contemplated that the foregoing discussion, protocols, and examples can be applied to therapy of other viruses through the administration of a variety of compounds, such as 2′,3′-dideoxyadenosine, that might cause neuropathy, hepatitis, or pancreatitis in human patients. The protocols described in the foregoing examples can also be used beneficially to optimize therapy with 2′,3′-dideoxyinosine in the treatment of cancer or certain other neoplasms, for example, neoplasms associated with AIDS. Patients with or without AIDS may show certain predispositions for a change in the clinical responses or adverse reactions to certain drugs when they have certain cancers or neoplasms. 2′,3′-Dideoxyinosine, for example, may be given to patients who have lymphoma, Kaposi's sarcoma, squamous cell carcinomas, and other forms of cancer or neoplasms. 2′,3′-Dideoxyinosine can also be used to treat human beings who have been infected with hepatitis-causing viruses and as above can be used in combination with other agents, such as alpha interferon, in such treatments as disclosed above. Also, various pharmaceutically acceptable 2′,3′-dideoxyinosine formulations may be administered such as esters and salts.

We claim:

1. A method for increasing the CD4 count or CD4+:CD8+ ratio in immunodepressed patients by administration of about 1.0 mg/kg/day to about 14 mg/kg/day of 2′,3′-dideoxyinosine.

2. A method of treating HIV infection which comprises administering to an HIV infected patient in need thereof about 0.4 to 25.6 mg/kg/day of 2′,3′-dideoxyinosine in combination with a member selected from the group consisting of 3′-azido-2′,3′-dideoxythymidine, acyclovir, gancyclovir, pentamidine and ribovirin.

3. A method of claim 2 wherein the 2′,3′-dideoxyinosine is administered in combination with 3′-azido-2′,3′-dideoxythymidine (AZT, zidovudine).

4. A method of claim 2 wherein the 2′,3′-dideoxyinosine is administered in combination with acyclovir.

5. A method of claim 2 wherein the 2′,3′-dideoxyinosine is administered in combination with gancyclovir.

6. A method of claim 2 wherein the 2′,3′-dideoxyinosine is administered in combination with pentamidine.

7. A method of claim 6 wherein the pentamidine is administered in dosage of about 50 to about 400 mg.

8. A method of claim 2 wherein the 2′,3′-dideoxyinosine is administered in combination with about 200 mg/day to about 1600 mg/day of ribavirin.

9. A method of administering 2′,3′-dideoxyinosine to a patient infected with HIV in a manner to minimize neuropathy comprising administration of 2′,3′-dideoxyinosine wherein the 2′,3′-dideoxyinosine is withheld at the first indication of pain, tingling, or a loss of vibratory sense, followed by a resumption of dosing with about 0.4 to about 9.6 mg/kg/day of 2′,3′-dideoxyinosine when the aforementioned symptoms and signs subside.

10. A method of administering 2′,3′-dideoxyinosine to a patient infected with HIV in a manner to minimize pancreatitis comprising administration of 2′,3′-dideoxyinosine in a range of about 0.4 mg/kg/day to about 14 mg/kg/day wherein:
   (1) the patient's serum triglyceride levels and/or serum amylase levels are monitored;
   (2) the 2′,3′-dideoxyinosine is withheld when the serum triglyceride level exceeds about 500 mg/dl or the amylase levels rise to about 150% or more of the upper limit of normal levels; and
   (3) administration of 2′,3′-dideoxyinosine is resumed at a dose of about 0.4 mg/kg/day to about 9.6 mg/kg/day after triglyceride or amylase levels return to about normal or baseline levels.

11. A method of administering 2′,3′-dideoxyinosine to a patient infected with HIV in a manner to minimize hepatitis comprising administration of 2′,3′-dideoxyinosine in a range of about 0.4 mg/kg/day to about 14 mg/kg/day wherein
   (1) the patient's hepatic transaminase levels are monitored;
   (2) the 2′,3′-dideoxyinosine is withheld when the transaminase levels exceed about five times the upper limit of normal; and
   (3) administration of 2′,3′-dideoxyinosine is resumed at a dose of about 0.4 mg/kg/day to about 9.6 mg/kg/day after the transaminase levels return to three times the upper limit of normal or lower.

12. A method of treating HIV infection which comprises administering to an HIV infected patient in need thereof 2',3'-dideoxyinosine (ddI) at a dose of about 0.4 to about 9.6 mg/kg/day.

13. The method according to claim 12, wherein said ddI is administered at a dose of about 3.2 to 9.6 mg/kg/day.

14. The method according to claim 12, wherein said ddI is administered at a dose of about 6.4 to 9.6 mg/kg/day.

15. The method according to claim 12, wherein said ddI is administered in multiple dosages per day.

16. A method of administering 2',3'-dideoxyinosine (ddI) to a patient infected with HIV in a manner to minimize treatment induced pancreatitis or other pancreatic dysfunction which comprises:
    (a) administering said ddI to said patient at a dosage of about 0.4 to about 25.6 mg/kg/day;
    (b) monitoring said patient for indications of an increased risk of pancreatitis or other pancreatic dysfunction;
    (c) interrupting the administration of said ddI when said indications are noted; and
    (d) resuming administration of said ddI at a dosage of about 0.4 to about 14 mg/kg/day when said indications subside.

17. The method according to claim 16, wherein said monitoring comprises monitoring the triglyceride levels of said patient and interrupting said administration of ddI when said triglyceride level indicates an increased risk of pancreatitis.

18. The method according to claim 16, wherein said ddI is administered at a dose of about 3.2 to about 9.6 mg/kg/day.

19. The method according to claim 16, wherein said ddI is administered in combination with a member selected from the group consisting of 3'-azido-2',3'-dideoxythymidine, acyclovir, gancyclovir, pentamidine and ribavirin.

20. A method of administering 2',3'-dideoxyinosine (ddI) to a patient infected with HIV in a manner to minimize treatment induced neuropathy which comprises:
    (a) administering said ddI to said patient at a dosage of about 0.4 to about 25.6 mg/kg/day;
    (b) monitoring said patient for indications of potential onset of neuropathy;
    (c) interrupting the administration of said ddI when said indications are noted; and
    (d) resuming administration of said ddI when said indications subside.

21. The method according to claim 20, wherein said monitoring comprises monitoring said patient for indications of pain, tingling or a loss of vibratory sense.

22. The method according to claim 20, wherein said ddI is administered at a dose of about 3.2 to about 9.6 mg/kg/day.

23. The method according to claim 20, wherein said ddI is administered in combination with a member selected from the group consisting of 3'-azido-2',3'-dideoxythymidine, acyclovir, gancyclovir, pentamidine and ribavirin.

24. A method of administering 2',3'-dideoxyinosine (ddI) to a patient infected with HIV in a manner to minimize treatment induced hepatitis which comprises:
    (a) administering said ddI to said patient at a dosage of about 0.4 to about 25.6 mg/kg/day;
    (b) monitoring said patient for indications of potential onset of hepatitis;
    (c) interrupting the administration of said ddI when said indications are noted; and
    (d) resuming administration of said ddI when said indications subside.

25. The method according to claim 24, wherein said monitoring comprises monitoring the hepatic transaminase levels of said patient and interrupting said administration of ddI when said transaminase level indicates a potential onset of hepatitis.

26. The method according to claim 24, wherein said ddI is administered at a dose of about 3.2 to about 9.6 mg/kg/day.

27. The method according to claim 24, wherein said ddI is administered in combination with a member selected from the group consisting of 3'-azido-2',3'-dideoxythymidine, acyclovir, gancyclovir, pentamidine and ribavirin.

* * * * *